United States Patent [19]

Lackney

[11] Patent Number: 5,223,259
[45] Date of Patent: Jun. 29, 1993

[54] SECURING MEANS FOR AN ORAL MEDICAMENT AND SUPPORT THEREFOR

[76] Inventor: Albert M. Lackney, 1795 T.R. 320 SE., Crooksville, Ohio 43731

[21] Appl. No.: 754,340

[22] Filed: Sep. 9, 1991

Related U.S. Application Data

[63] Continuation-in-part of Ser. No. 584,601, Sep. 19, 1990, Pat. No. 5,085,634.

[51] Int. Cl.$^5$ .............................................. A61J 7/00
[52] U.S. Cl. ................................. 424/435; 424/422; 424/440; 604/77
[58] Field of Search ................. 424/440, 439, 435; 604/77

[56] References Cited

U.S. PATENT DOCUMENTS

| 96,360 | 7/1935 | Wheeler | 424/440 |
|---|---|---|---|
| 132,267 | 5/1942 | Weise | 424/440 |
| D. 274,859 | 7/1984 | Harris et al. | D1/104 |
| 589,712 | 9/1897 | Fouquier | 604/77 |
| 988,120 | 3/1911 | Lott | 604/93 |
| 1,298,616 | 3/1919 | Wilson | 604/77 |
| 1,593,858 | 7/1926 | Venable | 294/5.5 |
| 1,720,190 | 7/1929 | Van Horne | 294/5.5 |
| 1,847,415 | 3/1932 | Snell | 208/76 |
| 1,867,945 | 7/1932 | Hunter | 294/5.5 |
| 2,491,274 | 12/1949 | McNeill | 604/1 |
| 2,803,550 | 8/1957 | Ackalusky | 426/134 |
| 2,857,908 | 10/1958 | Cornfield | 128/15 |
| 2,872,925 | 2/1959 | Lindahl | 604/77 |
| 2,950,200 | 8/1960 | Jones et al. | 426/91 |
| 3,426,755 | 2/1969 | Clegg | 604/77 |
| 3,875,940 | 4/1975 | Beuther | 604/77 |
| 3,943,928 | 3/1976 | Lariccia et al. | 128/15 |
| 4,041,937 | 8/1977 | Diaz | 128/15 |
| 4,365,631 | 12/1982 | Kline | 604/55 |
| 4,430,075 | 2/1984 | Urban et al. | 604/77 |
| 4,551,329 | 11/1985 | Harris et al. | 295/5.5 |
| 5,085,634 | 2/1992 | Lackney | 604/77 |

OTHER PUBLICATIONS

Dyer, "Medicated Candies", Q. S. Magazine, vol. No. 1-No. 4, Apr. 1952.

Primary Examiner—Thurman K. Page
Assistant Examiner—Raj Bawa
Attorney, Agent, or Firm—Killworth, Gottman, Hagan & Schaeff

[57] ABSTRACT

An oral medicament adapted to be administered on a support which allows sucking of the medicament while preventing inadvertent swallowing of the medicament in its entirety or in large pieces, as well as preventing accidental swallowing of the support is provided. The support includes a stick of flexible plastic material having first and second ends, and may include an interlocking mechanism for the attachment of a safety guard which provides protection against accidental swallowing of the support. The medicament is secured to the first end of the support in a way which forms interlocking bonds with the medicament and controls the degree to which the medicament may be dissolved by the user.

21 Claims, 8 Drawing Sheets

SECURING MEANS FOR AN ORAL MEDICAMENT AND SUPPORT THEREFOR

CROSS-REFERENCE TO RELATED APPLICATIONS

This application is a continuation-in-part of U.S. application Ser. No. 584,601 filed Sep. 19, 1990, now U.S. Pat. No. 5,085,634, issued Feb. 4, 1992 entitled MEDICAMENT AND SUPPORT, the disclosure of which is hereby incorporated by reference.

BACKGROUND OF THE INVENTION

This invention relates to the combination of an oral medicament and a support therefor, and more particularly to a means for securing a medicament to a support which facilitates sucking on the medicament while preventing the medicament from breaking off from the support in its entirety or in large pieces which could cause choking, and further to a support which provides protection against accidental swallowing.

There are several types of common medicaments which are intended to be sucked or dissolved slowly in the mouth rather than swallowed whole like a pill. Such medicaments include cough drops, throat lozenges, and the like. However, such forms of medication may be unsuitable for small children or older patients, as large pieces of the medication might dissolve free and become lodged in the throat, causing choking. Additionally, the medication could accidentally be swallowed whole, causing choking or blockage of the throat cavity.

A solution to this problem is to supply the medication in the form of a lollipop or sucker in which the body of the medicament is secured to the end of a stick to facilitate sucking or chewing on the medication. If the medicament is not adequately secured to the stick, it may become separated from the stick and swallowed whole. A danger also exists in that if the user were in a reclined position while holding the stick, the stick could become lodged in the throat.

Several attempts have been made to overcome these problems. For example, Snell, U.S. Pat. No. 1,847,415, relates to a holder for candy suckers in which a guard at the upper end is embedded in the candy. The support for the candy comprises a flexible, bendable wire so that if the user would happen to fall while sucking on the stick, the flexible support would prevent the stick from becoming lodged in the throat. However, large pieces of the candy may still be able to break off from the wire and could become lodged in the throat.

Cornfield U.S. Pat. No. 2,857,908 describes a tongue depressor which is coated with a candied confection. The depressor is shown to contain three holes in its upper portion where the candy is secured to the depressor. However, there are still large areas where the candy remains unsecured and could become free of the depressor. The holes are only effective if both sides of the medication remain and work as a unit. For example, if the lower portion were to dissolve first, the upper portion would be able to break off. Further, there is no safety feature on the stick which would prevent the stick from becoming lodged in the throat.

Harris et al, U.S. Pat. No. 4,551,329 describes an oral medicament in a lollipop shape which is supported on a handle comprising a stick of resilient material looped into a single coil with spring arms extending into enlarged ears on which the medicament is molded. The handle is designed such that if the medicament becomes separated from the ears, the released spring arms will spring apart to block entry of the handle into the throat. However, there is a possibility that large pieces of the medicament could break off from the stick and, due to the spring action, be propelled and lodged in the throat. Further, there is no safety feature on the stick which would block entry of the handle into the throat while the medicament is secured to the stick.

Accordingly, there remains a need in the art for an oral medicament which may be administered on a support without the problem of the medication breaking off in its entirety or in large pieces, and further prevents the support from becoming lodged in the throat.

SUMMARY OF THE INVENTION

The present invention meets that need by providing a means for securing an oral medicament to a support which allows sucking of the medicament while preventing inadvertent swallowing of the medicament in its entirety or in large pieces, as well as preventing accidental swallowing of the support.

According to one aspect of the present invention, a solid medicament and a support in combination for oral administration of the medicament to a patient is provided. The combination comprises an elongated support having first and second ends, a solid medicament, and means for securing the medicament to one end of the support so that the medicament substantially covers the end of the support. The securing means also includes means for forming multiple interlocking bonds between the support and the medicament to prevent separation of the medicament from the support during oral administration of the medicament. The means for forming the interlocking bonds also act to control the degree to which the medicament can be dissolved by the user.

In one embodiment of the invention, the means for securing the medicament to the support comprises a plurality of bristles extending radially outward from the first end of the support. Preferably, the medicament is formed around the bristles such that the medicament substantially covers the end of the support.

In another embodiment of the invention, the securing means comprises a plurality of flattened disks spaced along the first end of the support, wherein each of the disks have a plurality of orifices therein to form interlocking bonds with the medicament. Preferably, the disks are generally circular and may vary in diameter.

In yet another embodiment of the invention, the securing means comprises a series of curved rib elements spaced around the first end of the support such that the spaces between the ribs permit the formation of interlocking bonds between the ribs and the medicament.

In still another embodiment of the invention, the securing means comprises a spiral-threaded element formed around the first end of the support, the threads forming interlocking bonds with the medicament. The threads may have orifices therein to enhance the bonding of the medicament to the support. The threads also control the degree to which the medicament is dissolved.

In a preferred process of the invention, the medicament in liquid form may be poured in and around the securing means and solidified to substantially cover the securing means as well as the end of the support. Thus, the medicament forms interlocking bonds with the securing means and is held securely to the support, preventing the medicament from breaking off in its entirety and preventing large pieces from breaking off. The medicament will be slowly dissolved in the mouth of the user.

Optionally, the support includes a detachable safety guard for preventing inadvertent swallowing of the support. The safety guard comprises a member having a slit therein for slidable attachment to the support. The support includes an interlocking means for securing the safety guard. In one embodiment of the invention, the slit on the safety guard includes a pair of opposing tabs which flex in only one direction, and the securing means on the support comprises a conical element adjacent a shield. The tabs on the safety guard are adapted to flex and permit the safety guard to slide over the conical element and lock into position against the shield. Alternatively, the securing means on the support comprises a flexible conical element adjacent a shield, and the safety guard is adapted to slide over the flexible conical element, temporarily collapsing it, and lock into position against the shield.

In a further embodiment of the invention, the support comprises a generally flat stick having a first end and a second end having a rounded edge, the first end including a generally flat disc including at least one raised area attached thereto. The medicament, in a disc-shaped form, may be secured to the front and/or back sides of the disc through indentations on the surface of the medicament which mate with the raised area on the disc. In a preferred form of the invention, the raised area is a rib or ring. The medicament may be secured to the disc by bonding or gluing using a food grade adhesive. The support may also include a notched edge for securing a safety guard as well as a hole on its lower portion to provide a means for grasping the support in the event of an accident.

In yet another embodiment of the invention, the oral medicament secured to the support includes means for preventing large pieces of the medicament from breaking off if accidentally bitten or chewed by the user. Preferably, at least a portion of the medicament is formed with a series of spaces therebetween so that upon biting, only small pieces of the medicament break off. In an alternative embodiment, the solid medicament includes break lines through at least a portion of the medicament which permits the medicament to break into small pieces upon biting. By break lines, it is meant that weakened areas are provided through at least a portion of the medicament so that when pressure is applied (from biting), the medicament breaks or fractures into small pieces.

Accordingly, it is an object of the present invention to provide means for securing an oral medicament to a support which allows sucking of the medicament while preventing accidental swallowing of the medicament in its entirety or in large pieces, as well as preventing accidental swallowing of the support. Other objects and advantages of the invention will be apparent from the following description, the accompanying drawings and the appended claims.

DETAILED DESCRIPTION OF THE PREFERRED EMBODIMENTS

Figure 1:
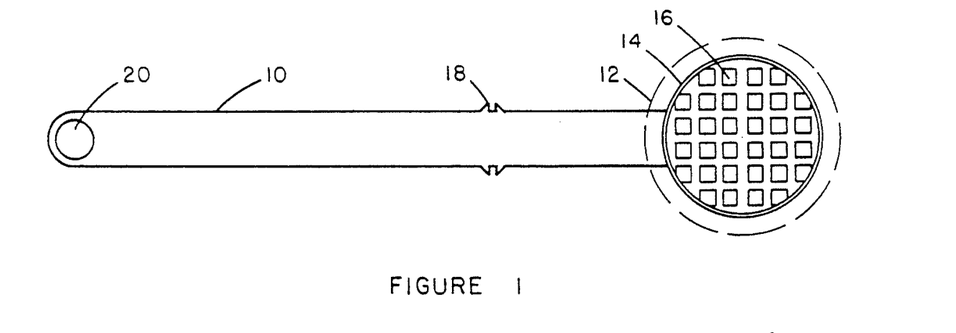
FIG. 1 is a top plan view of a medicament on a support in accordance with one embodiment of the present invention.

Reference is made to FIG. 1 of the drawings which illustrates the oral medicament secured to a support. In accordance with the present invention, an elongated support 10 is provided which includes means for securing a solid medicament 12 thereto. In this embodiment, the support comprises a generally flat stick having a first end and a second end having a rounded edge. The support preferably comprises a flexible plastic material and can be molded as a unitary structure using techniques known in the art.

Figure 3:
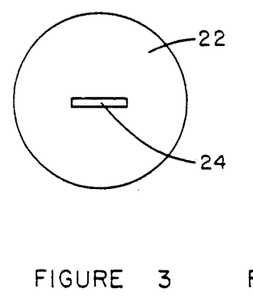
FIG. 3 is a plan view of the safety guard of the present invention.

The support 10 also optionally includes notched edge 18 for securing the removable safety guard shown in FIG. 3. The second end of the support also includes a hole 20 for the purpose of providing a means for grasping or hooking onto the support in the event of an accidental swallowing.

Figure 2:
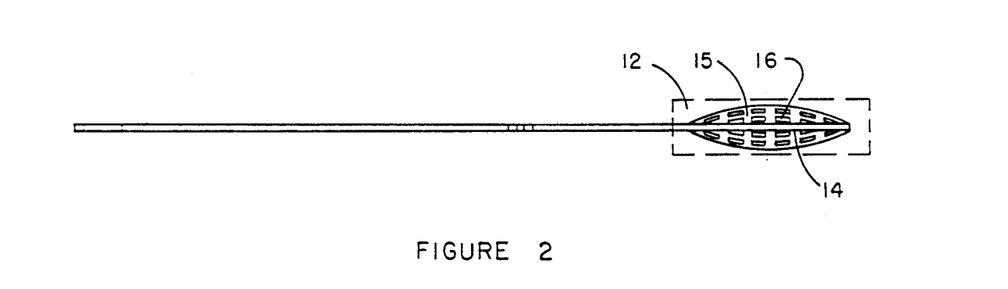
FIG. 2 is a side view of the medicament on the support of FIG. 1.

In the embodiment shown in FIGS. 1 and 2, the medicament 12 is attached to the support 10 by a flattened spherical frame 14 which is attached to the support. Preferably, the frame and support both comprise a flexible plastic material which can be molded as a unitary structure. The flattened spherical frame comprises a cavity 15 and a plurality of crosshatched holes 16 on the surface thereof. The medicament may be poured in a liquid state through the holes of the frame and solidified in a mold or by other means so as to completely fill the cavity and cover the frame. This is illustrated in the side view of the support shown in FIG. 2. The spherical frame and holes act to form multiple interlocking bonds with the medicament, thus preventing separation of the medicament from the support as well as preventing breakage (through the dissolving process) of any large pieces away from the support. For example, if the lower portion of the medicament were to dissolve first, the upper portion would remain secured due to a core of the medicament (formed within spherical frame 14) remaining within cavity 15.

Figure 4:
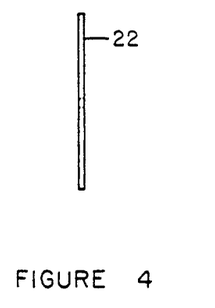
FIG. 4 is a side view of the safety guard.
Figure 5:
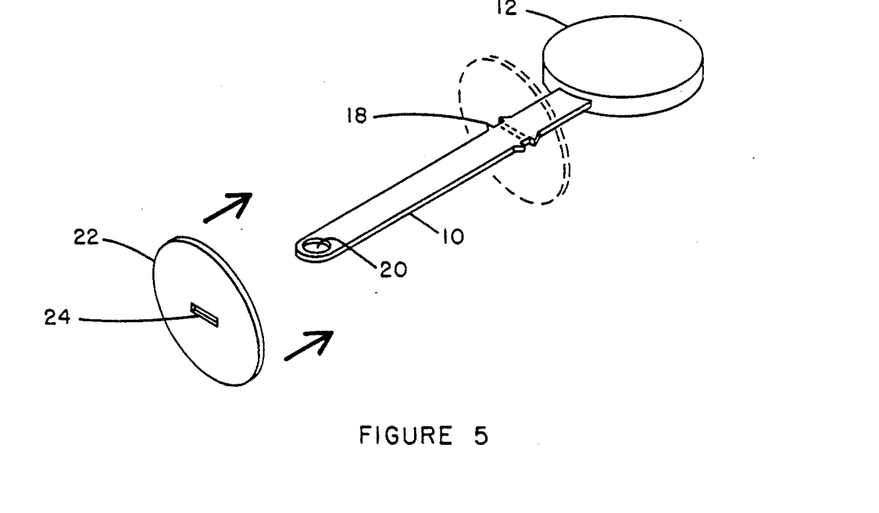
FIG. 5 is a perspective view of the medicament on the support illustrating the use of the safety guard.

FIGS. 3 and 4 illustrate the optional safety guard 22 which may be slidably attached to support 10 in order to provide a protective means which prevents the support from being forced into the user's throat. The safety guard comprises a generally round plate 22 with a slit 24 in its middle portion. As illustrated in FIG. 5, the safety guard may be mounted on the support 10 by slidably attaching it to notched edge 18 of the support where it becomes locked into place. Guard 22 may also be fabricated of a flexible plastic material.

Figure 6:
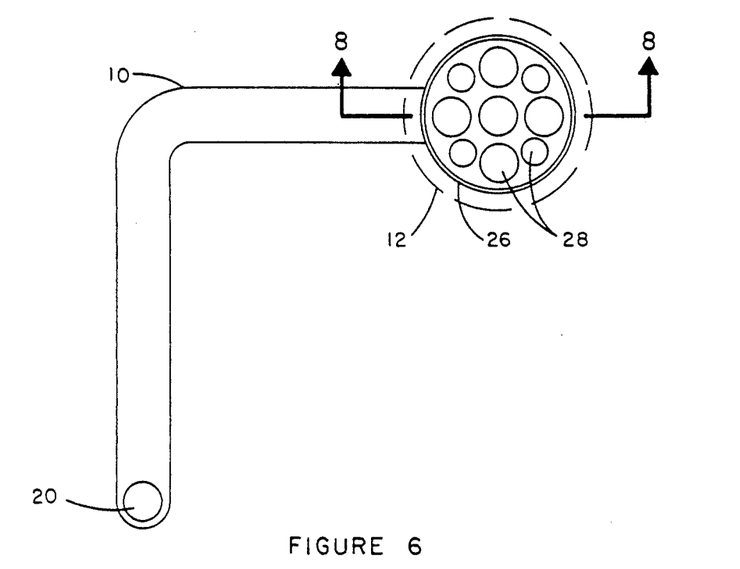
FIG. 6 is a top plan view of another embodiment of the invention.

Another embodiment of the invention is illustrated in FIG. 6 in which the support comprises a generally flat stick having a first end and a second end having a rounded edge. The support 10 is turned at an angle, preferably a right angle as illustrated, at its middle portion to prevent the support from being accidentally swallowed or forced down the throat of a user. A generally circular frame 26 is attached to the support on its first end and includes a plurality of raised pedestals 28 attached to the frame into which the liquid medicament may be poured and solidified. The support also includes a hole 20 on its lower portion to provide a means for grasping the support in the event of accidental swallowing. As will be appreciated, this angled support may be used with any of the other embodiments of the invention. Additionally, the angle may also be formed by bending the support. This may be facilitated by providing a weakened area or notched area across the width of the support so that the support will bend along that line. Further, locking means may be provided to lock the support in an angled position. The locking means may comprise, for example, a pair of interlocking tabs or ribs on the support.

Figure 7:
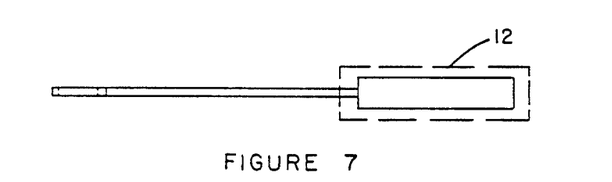
FIG. 7 illustrates a side view of the solid medicament secured to the circular frame of FIG. 6.
Figure 8:
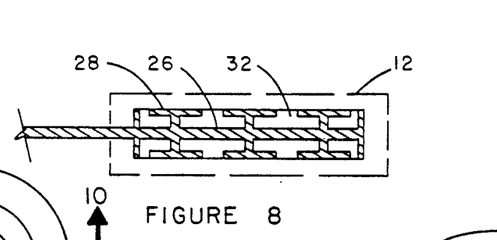
FIG. 8 is a sectional view of the circular frame taken along line 8—8 in FIG. 6.

FIG. 8 illustrates a sectional side view of the circular frame 26. As can be seen, the raised circular pedestals 28 create a cavity 32 into which the medicament may be poured. As shown in FIG. 7, the frame becomes completely coated with the solid medicament, thus forming multiple interlocking bonds which prevent separation of the medicament from the support as well as preventing breakage of any large pieces away from the support.

Figure 9:
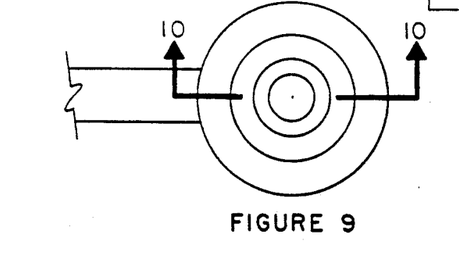
FIG. 9 is a top plan view of another embodiment of the invention.
Figure 10:
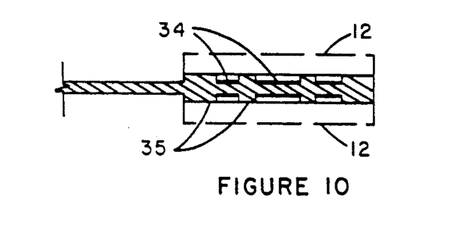
FIG. 10 is a partial side view taken along line 10—10 in FIG. 9.
Figure 11:
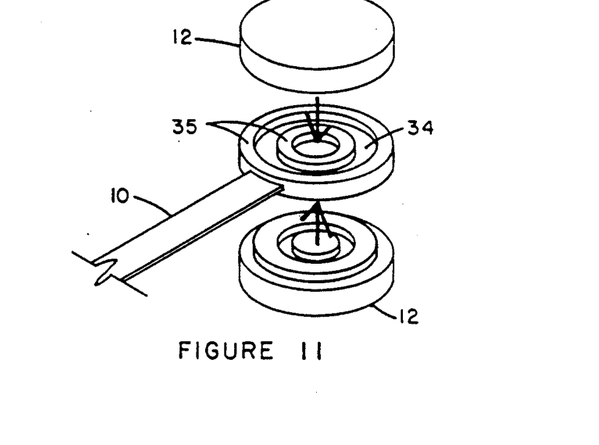
FIG. 11 is a partial perspective of the embodiment of FIGS. 9 and 10 and illustrates placement and mating of the medicament with raised areas on the disc.

FIGS. 9 through 11 illustrate yet another embodiment of the invention in which the support comprises a generally flat stick 10 as described above. Attached to the stick is a generally flat disc 34 with raised areas 35 which serve as a means for securing the medicament to the disc. As shown, these raised areas 35 may take the form of raised rings or ribs. The medicament may take the form of discs or lozenges 12, each preferably having the same diameter as the flat disc 34 and with matching indentations as the raised areas 35. The medicament discs may be secured to disc 34 with the use of a food-grade glue or other adhesive applied only the portion of medicament disc 12 making contact with disc 34. This prevents the user from dissolving the medicament to within the area of the applied glue.

Figure 12:
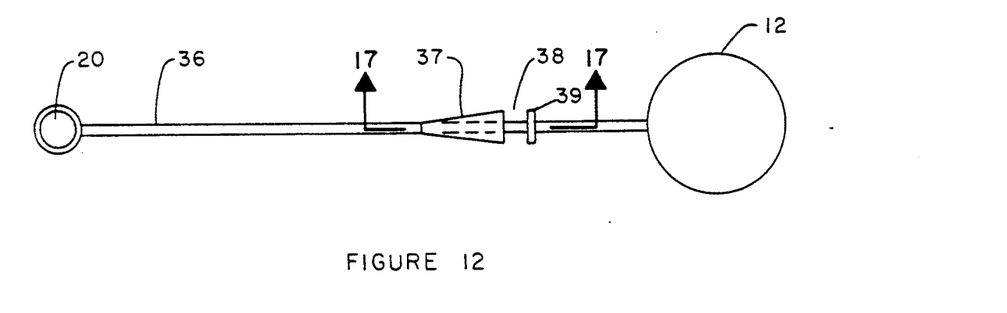
FIG. 12 is a top plan view of a medicament on a support illustrating the interlocking means on the support.
Figure 13:
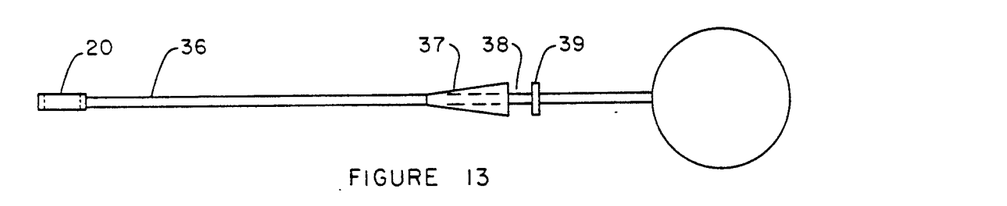
FIG. 13 is a side view of the embodiment shown in FIG. 12.

FIGS. 12 and 13 illustrate another embodiment of the invention in which the medicament 12 is secured to the support 36 which includes interlocking means for securing a safety guard comprising a flexible conical element 37 and a generally circular shield 39. In this embodiment, support 36 is shown as having a generally circular cross section. The safety guard is attached to the support by sliding it over the conical element which flexes and temporarily collapses to permit the safety guard to slide over it. The shield 39 then acts to lock the safety guard into place, and the conical element regains its original shape.

Figures 14, 15, 16, 17:
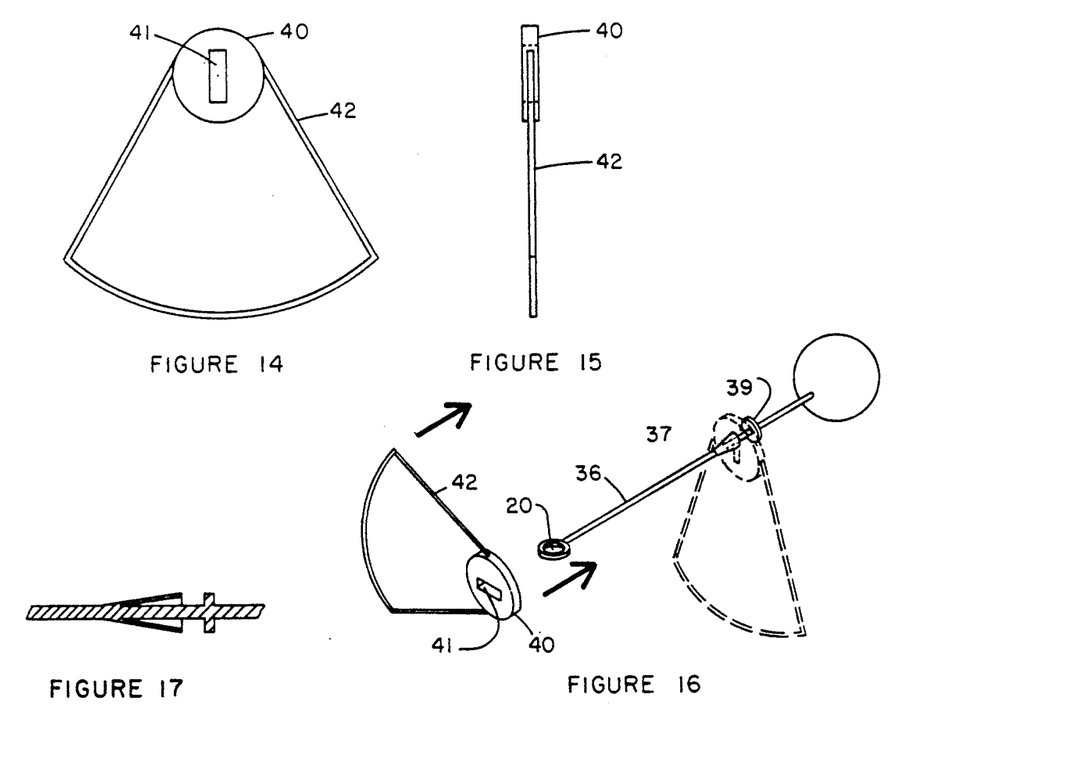
FIG. 14 is a plan view illustrating another embodiment of the safety guard.
FIG. 15 is a side view of the safety guard of FIG. 14.
FIG. 16 is a perspective view of the medicament on the support illustrating installation of the safety guard.
FIG. 17 is a sectional view taken along line 17—17 in FIG. 12 showing the collapsible conical interlocking element.

FIGS. 14 and 15 illustrate one form of the detachable safety guard 40 having a slit 41 in its center portion and also having an optional handle portion 42 attached to opposing sides of the guard. As illustrated in FIG. 16, the safety guard may be mounted onto support 36 by sliding it over conical element 37 and locking it into position against shield 39.

Figures 28, 29, 30:
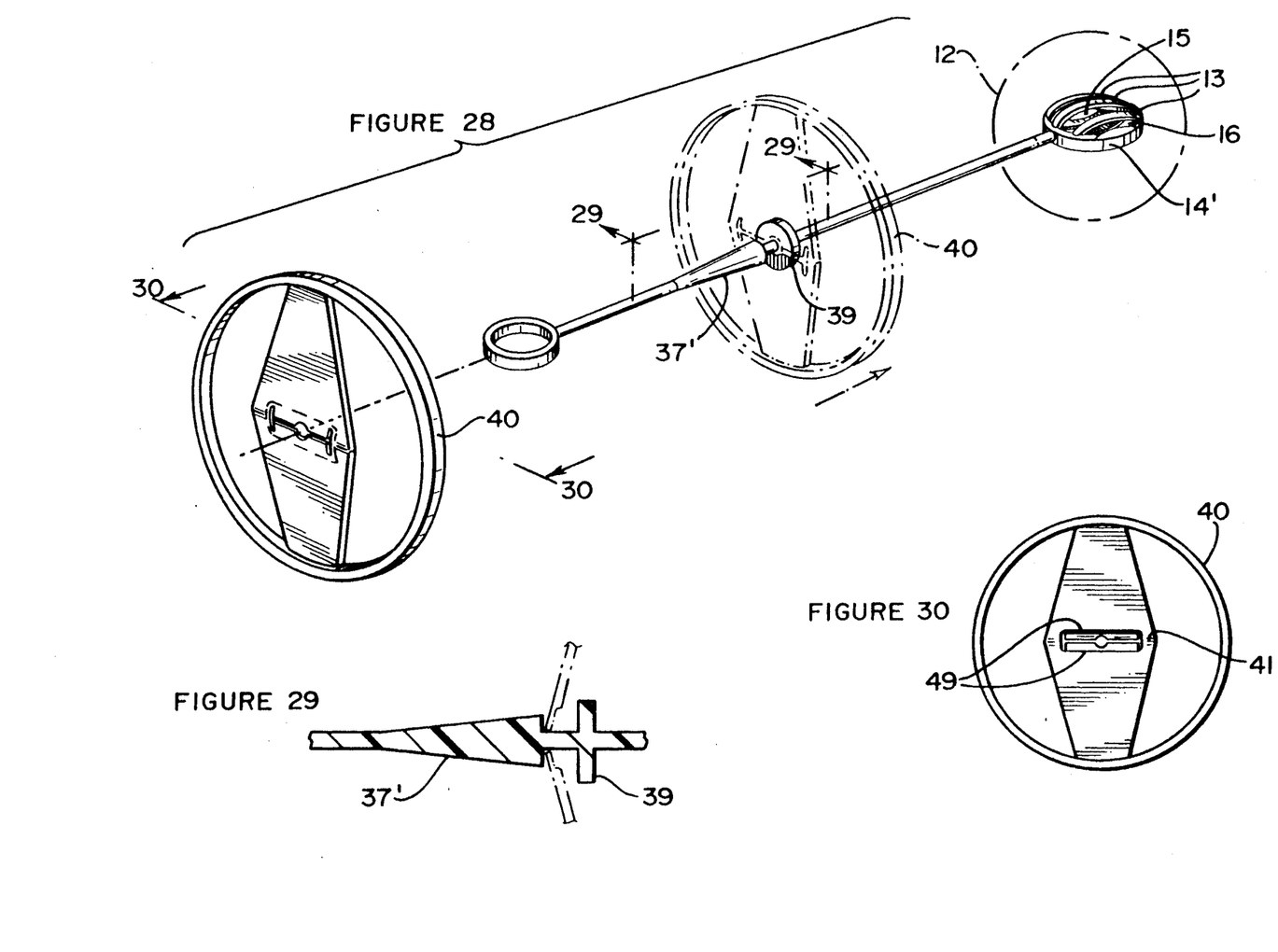
FIG. 28 is a perspective view of the medicament on the support illustrating installation of the safety guard having flexible tabs.
FIG. 29 is a sectional view of the solid conical interlocking element taken along line 29—29 in FIG. 28.
FIG. 30 is a plan view illustrating the safety guard shown in FIG. 28.

FIGS. 28–30 show an alternate construction for safety guard 40 and conical element 37'. As shown in FIG. 30, the slit 41 on the safety guard 40 may include a pair of opposing tabs 49. The tabs on the safety guard are adapted to flex in only one direction and permit the safety guard to slide over a solid conical element 37' and lock into position against shield 39 of the support as shown in FIG. 28.

FIG. 28 also illustrates another embodiment of the interlocking means for the medicament as used in the present invention. As shown, medicament 12 (shown in phantom) is secured to a hollow circular frame 14' which has a plurality of ribs 13 spanning the frame.

Figure 18:
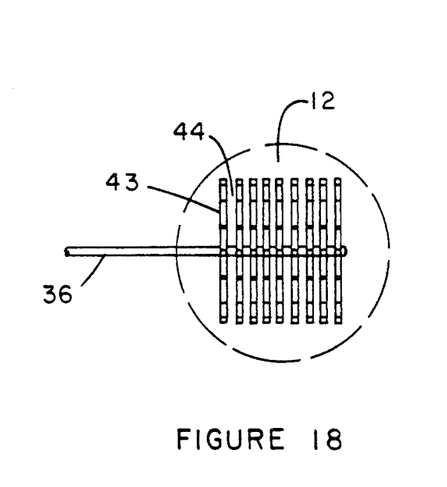
FIG. 18 is a partial side view of another embodiment of the invention utilizing radially extending bristles.
Figure 19:
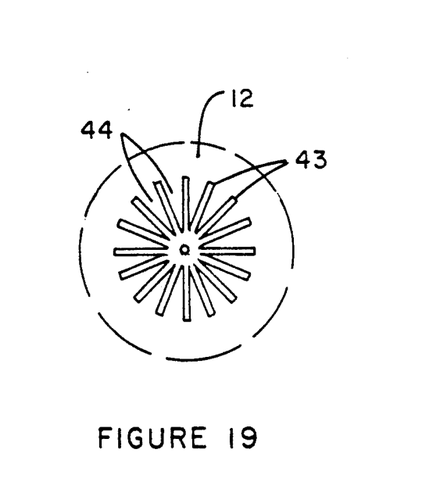
FIG. 19 is an end view of the securing means shown in FIG. 18.
Figure 20:
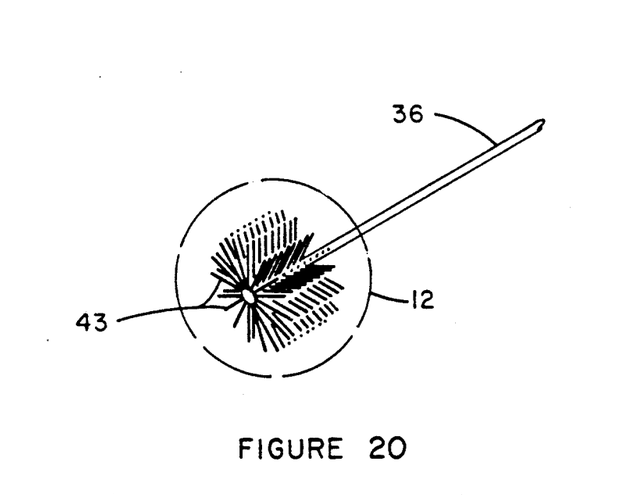
FIG. 20 is a perspective view of the securing means of FIG. 18 attached to the support.
Figure 21:
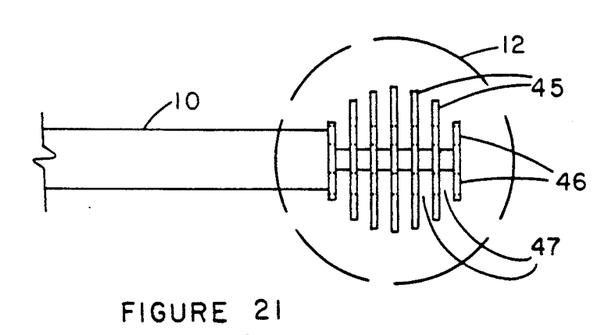
FIG. 21 is a partial top plan view of another embodiment of the invention.

FIGS. 18–20 illustrate another embodiment of the invention in which the means for securing the medicament comprises a plurality of bristles 43 extending radially outward from the first end of the support. The bristles may be formed from a thermoplastic material. Preferably, the medicament 12 is poured in liquid form around the bristles such that the medicament substantially covers the end of the support. After solidification, the bristles 43 form multiple interlocking bonds with the medicament and serve to control the degree to which the medicament can be dissolved by the user.

Figure 25:
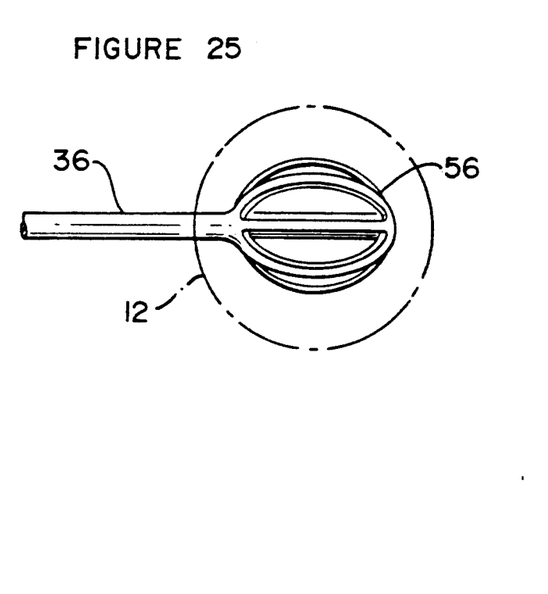
FIG. 25 is a plan view illustrating another embodiment of the invention in which the interlocking means on the support comprise curved ribs.
Figure 26:
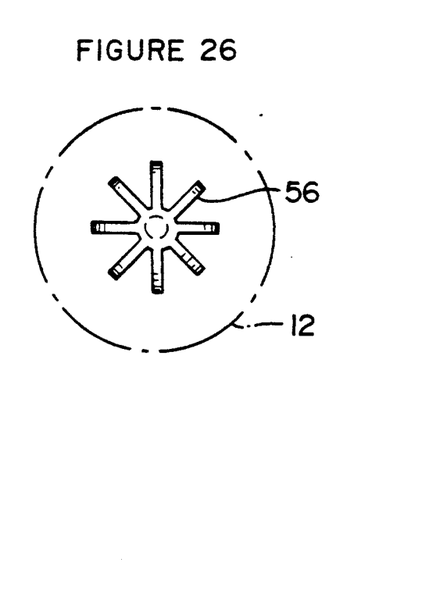
FIG. 26 is an end plan view illustrating the embodiment shown in FIG. 25.

FIGS. 25 and 26 illustrate another embodiment of the invention in which the securing means comprises a series of curved rib elements 56 spaced around the first end of the support which form interlocking bonds with the medicament. The curved ribs also act to control the degree to which the medicament can be dissolved.

Figure 27:
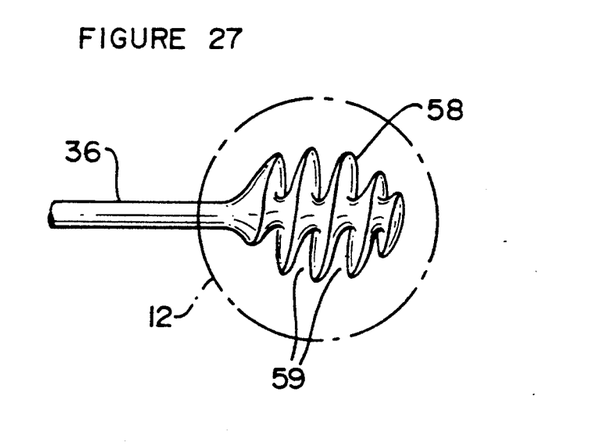
FIG. 27 is a plan view illustrating another embodiment of the invention.

FIG. 27 illustrates another embodiment in which the securing means comprises a threaded spiral element 58 formed around the first end of the support, the threads of which form interlocking bonds with the medicament and control the degree to which the medicament can be dissolved. Spiral element 58 may have orifices 59 therein to enhance the bonding of the medicament to the support.

Figures 22, 23:
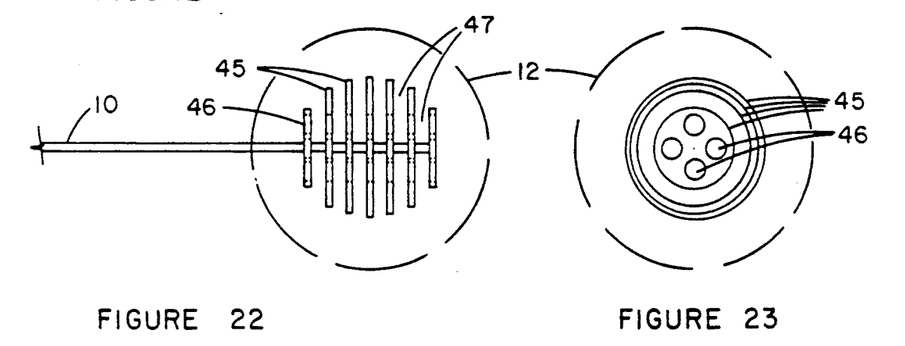
FIG. 22 is a side view of the securing means shown in FIG. 21.
FIG. 23 is an end view of the securing means.
Figure 24:
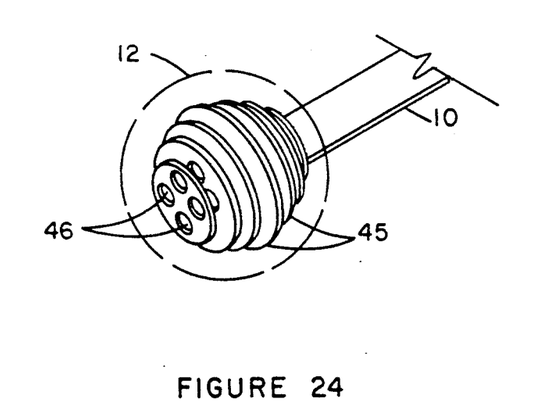
FIG. 24 is a partial perspective view of the securing means of FIGS. 21-23 attached to the support.
Figure 31:
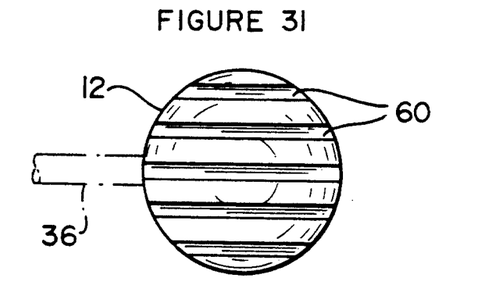
FIG. 31 is a top plan view of another embodiment of the invention.
Figure 32:
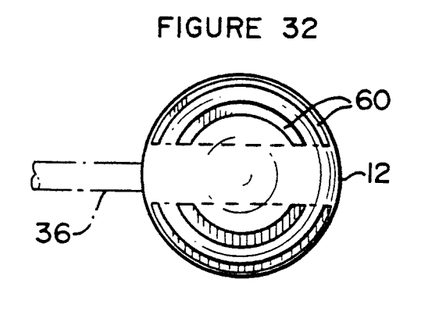
FIG. 32 is a side view of the medicament illustrated in FIG. 32.
Figure 33:
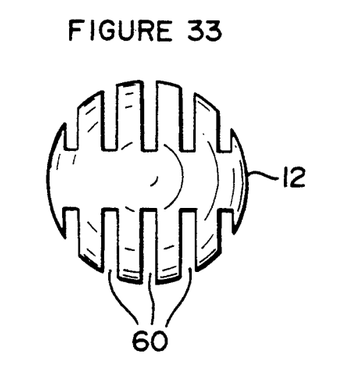
FIG. 33 is an end view of the medicament illustrated in FIG. 32.

FIGS. 21-24 illustrate yet another embodiment of the invention wherein the securing means comprises a plurality of generally circular flattened disks 45 spaced along the first end of the support. As shown in FIGS. 23 and 24, each of the disks include a plurality of orifices 46 which form interlocking bonds with the medicament. These disks also control the degree to which the medicament can be dissolved. FIGS. 31-33 illustrate another embodiment of the invention wherein the medicament 12 includes means for preventing large pieces of said medicament from breaking off when the medicament is accidentally bitten. As shown in FIG. 33, at least a portion of the medicament is provided with a series of spaces 60 therebetween so that upon biting or chewing, the medicament breaks into small pieces. Such spaces may be provided by using a shaped mold having a series of spaced walls around which liquid medicament is poured and then solidified.

Figure 34:
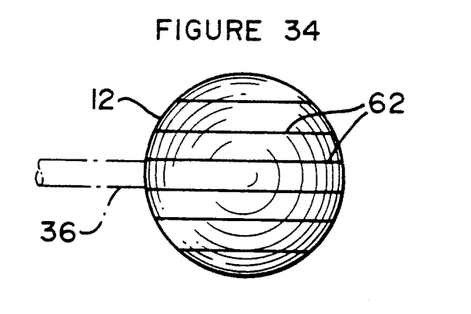
FIG. 34 is a top plan view of a medicament in another embodiment of the invention.
Figure 35:
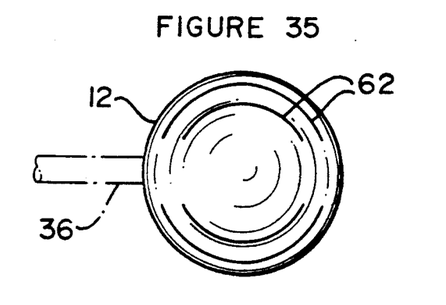
FIG. 35 is a side view of the medicament and support illustrated in FIG. 35.
Figure 36:
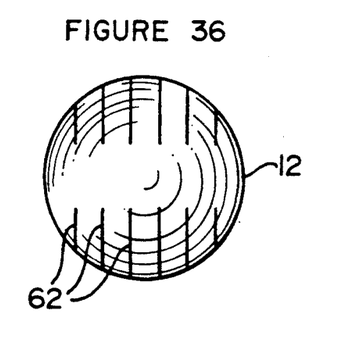
FIG. 36 is an end view of the medicament illustrated in FIG. 35.

As shown in FIGS. 34-36, the solid medicament may alternatively be formed by a process which results in the formation of break lines 62 along the medicament which causes the medicament to break into small pieces upon biting or chewing. Such break lines or weakened areas may be formed by casting a liquid medicament in stages, permitting one stage to harden or set prior to casting the succeeding stage.

It will be apparent to those skilled in the art that several different combinations of the above embodiments are possible to produce the desired features previously described.

Having described the invention in detail and by reference to preferred embodiments thereof, it will be apparent that modifications and variations are possible without departing from the scope of the invention defined in the appended claims.

What is claimed is:

1. In combination, a solid medicament and support for oral administration of said medicament to a patient comprising:
   a) an elongated support having first and second ends;
   b) a solid medicament; and
   c) means for securing said medicament to one end of said support so that said medicament is firmly secured to said end of said support, said securing means including means for forming multiple interlocking bonds between said support and said medicament to prevent separation of said medicament from said support during oral administration thereof.

2. The combination of claim 1 wherein said securing means comprises a plurality of bristles extending radially outward from said first end of said support.

3. The combination of claim 1 wherein said securing means comprises a plurality of flattened disks spaced along said first end of said support, wherein each of said disks have a plurality of orifices therein to form said interlocking bonds with said medicament.

4. The combination of claim 3 wherein said disks are generally circular and vary in diameter.

5. The combination of claim 4 wherein said disks are arranged along said support such that said disks at opposite ends are smaller than those in the central portion.

6. The combination of claim 1 wherein said securing means comprises a series of curved rib elements spaced around the first end of said support such that the spaces between said ribs permit the formation of interlocking bonds between said ribs and said medicament.

7. The combination of claim 1 wherein said securing means comprises a spiral-threaded element formed around said first end of said support, said threads forming interlocking bonds with said medicament.

8. The combination of claim 7 wherein said threads have orifices therein to enhance bonding of said medicament to said support.

9. In combination, an oral medicament secured to a support comprising:
   a) an elongated support having first and second ends; and
   b) a solid oral medicament secured to one end of said support, wherein said medicament includes means for preventing pieces of said medicament of a size which could cause choking or lodge in the throat of a user from breaking off.

10. The combination of claim 9 wherein at least a portion of said solid medicament is formed with a series of spaces therebetween.

11. The combination of claim 9 wherein said solid medicament includes break lines through at least a portion thereof.

12. In combination, an oral medicament secured to a support comprising:
   a) an elongated support having first and second ends including means for securing a solid oral medicament thereto, said securing means comprising:
   a flat disk having a front side and a back side, said disk attached to said first end of said support for securing said medicament;
   b) a solid oral medicament secured to said front and back sides of said disk and substantially covering said disk, said disk including at least one raised area which mates with a corresponding indentation on said solid medicament for securing said medicament to said disk;
   whereby said oral medicament secured to said support allows sucking of said medicament while preventing inadvertent swallowing of said medicament or said support.

13. The combination of claim 12 wherein said support has a notched edge adjacent said disk and means for grasping said support on said second end.

14. The combination of claim 12 wherein said support includes a safety guard comprising a rounded plate with a slit in its middle portion for slidably attaching said guard to said notched edge on said support.

15. The combination of claim 14 wherein said support comprises a flexible plastic material.

16. The combination of claim 12 wherein said at least one raised area on said disk is a raised ring.

17. In combination, a support for oral administration of a medicament and a safety guard comprising:
   an elongated support;
   a detachable safety guard for preventing inadvertent swallowing of said support comprising a member having a slit therein for slidable attachment to said support; and
   means on said support for slidably securing said safety guard thereto comprising means for interlocking with said slit.

18. The support of claim 17 wherein said safety guard further comprises a handle portion attached to opposing sides of said safety guard.

19. The elongated support of claim 17 wherein said slit includes a pair of opposing tabs which flex in only one direction.

20. The support of claim 19 wherein said interlocking means on said support comprises a conical element adjacent a shield, said tabs on said safety guard adapted to flex and permit said safety guard to slide over said conical element and lock into position against said shield.

21. The support of claim 17 wherein said interlocking means on said support comprise a flexible conical element adjacent a shield, said safety guard adapted to slide over said conical element and lock into position against said shield.

* * * * *